United States Patent [19]

Higuchi et al.

[11] 4,285,947

[45] Aug. 25, 1981

[54] ALDEHYDE ADDUCTS OF TRIAMTERENE

[75] Inventors: Takeru Higuchi; Anand C. Burman, both of Lawrence, Kans.

[73] Assignee: INTERx Research Corporation, Lawrence, Kans.

[21] Appl. No.: 113,313

[22] Filed: Jan. 18, 1980

[51] Int. Cl.³ .......................................... C07D 475/08
[52] U.S. Cl. ................................... 424/251; 544/260
[58] Field of Search ................ 544/277, 260; 424/251

[56] References Cited

U.S. PATENT DOCUMENTS

3,081,230  3/1963  Weinstock et al. .................. 424/251

*Primary Examiner*—Nicholas S. Rizzo
*Attorney, Agent, or Firm*—Burns, Doane, Swecker & Mathis

[57] ABSTRACT

The invention provides novel aldehyde adducts of triamterene having improved solubility and bioavailability as compared to triamterene. Pharmaceutical compositions containing the novel adducts and having diuretic activity are also described.

60 Claims, 4 Drawing Figures

ALDEHYDE ADDUCTS OF TRIAMTERENE

BACKGROUND OF THE INVENTION

1. Field of the Invention

The invention relates to novel aldehyde adducts of triamterene, to pharmaceutical compositions containing said adducts and to methods of administering same to mammals to elicit a diuretic response therein without substantial loss of potassium.

2. Description of the Prior Art

Triamterene, also known as 2,4,7-triamino-6-phenylpteridine, is a well-known pteridine diuretic having the structural formula:

The diuretic, hypotensive and potassium-saving properties of triamterene, when used alone or in combination with other diuretics, has been known for some time. (See, for example, Weinstock et al U.S. Pat. No. 3,081,230, hereby incorporated by reference herein in its entirety and relied upon.) Triamterene is currently marketed as DYRENIUM ®, in which it is the sole active ingredient, and in a combination with hydrochlorothiazide available under the name DYAZIDE ®. The drug is widely used, particularly for its ability to restrict the loss of potassium caused by other diuretics. Unfortunately, as has been shown previously, e.g., *Clin. Pharmacol. & Ther.* 21, 610 (1977), the plasma and the urine concentration of triamterene following the recommended clinical dose is extremely low, due to incomplete absorption. The bioavailability of the drug, based on the urinary concentration of the drug and its metabolite, has been found to vary between 30% and 70%. The low aqueous solubility of this compound, i.e., 45 $\mu$g/ml, as reported in *J. Pharm. Sci.* 53, 1325 (1964), as well as its limited solubility in lipid-like solvents, is primarily responsible for its impaired dissolution in vivo, and hence, its complete absorption. Accordingly, a clear need exists for a means of effectively increasing the solubility, and hence the bioavailability, of triamterene.

SUMMARY OF THE INVENTION

A primary object of the present invention is to provide a novel class of compounds which are aldehyde adducts of triamterene.

A further object of the present invention is to effectively increase the solubility, and hence the bioavailability, of triamterene by forming soluble derivatives which will rapidly dissociate back to triamterene when absorbed.

Still another object of the present invention is to provide a novel group of aldehyde adducts of triamterene which can be administered to warm-blooded animals in compositions capable of eliciting a diuretic response without accompanying substantial loss of potassium.

Yet another object of the invention is to provide a novel class of compounds which will elicit a more effective response, at lower concentrations or dosage levels, then their parent compound, triamterene.

In accord with the foregoing objects, the present invention provides novel aldehyde adducts of triameterene having the formula:

wherein R is selected from the group consisting of:
hydrogen;
alkyl of 1 to 20 carbon atoms;
cycloalkyl of 3 to 8 carbon atoms;
aryl of 6 to 10 carbon atoms;
alkenyl of 2 to 20 carbon atoms;
alkynyl of 2 to 20 carbon atoms;
cycloalkenyl of 4 to 8 carbon atoms;
acyl of 1 to 22 carbon atoms;
mono- and poly-substituted aryl wherein aryl is as defined above and wherein the substituents, which may be the same or different, are such selected from the group consisting of lower alkylthio, lower alkyl, halo, lower alkoxy, nitro, cyano, lower alkanoyl, lower carbalkoxy, di(lower alkyl)amino, lower alkanoyloxy, lower haloalkyl, lower alkylsulfonyl, hydroxy, lower hydroxyalkyl, amino, lower alkanoylamino, lower alkylamino, carboxyl, lower carboxyalkyl, carbamoyl, lower alkylcarbamoyl, di(lower alkyl)carbamoyl, lower alkyl, lower alkynyl, oxo, and —alkylene—aryl wherein the aryl portion contains 6 to 10 carbon atoms and the alkylene portion contains up to 6 carbon atoms;

mono- and poly-substituted alkyl, cycloalkyl, alkenyl, alkynyl and cycloalkenyl wherein alkyl, cycloalkyl, alkenyl, alkynyl and cycloalkenyl are as defined above with respect to R and wherein the substituents, which may be the same or different, are each selected from the group consisting of halo, hydroxy, lower alkoxy, carboxy, oxo, lower alkanoyloxy, aryloxy of 6 to 10 carbon atoms and mono- and poly-substituted aryloxy wherein mono- and poly-substituted aryl are defined as hereinabove;

saturated and unsaturated monoheterocyclic, polyheterocyclic and fused heterocyclic groups containing from 1 to 3 of any one or more of the hetero atoms N, S and O in each heterocyclic ring thereof and each such ring being 3- to 8-membered;

mono- and poly-substituted derivatives of the aforesaid monoheterocyclic, polyheterocyclic and fused heterocyclic groups wherein the substituents, which may be the same or different, are each selected from the group consisting of lower alkyl, lower haloalkyl, halo, amino, oxo, nitro, hydroxy, lower hydroxyalkyl, carboxyl, lower carboxyalkyl, lower alkanoylamino, lower alkoxy, lower alkanoyl, lower alkanoyloxy, cyano, lower carbalkoxy, lower alkylthio, lower alkylamino, di(lower alkyl)amino, carbamoyl, lower alkylcarbamoyl, di(lower alkyl)carbamoyl, lower alkenyl, lower alkynyl, lower alkylsulfonyl, aryl of 6 to 10 carbon atoms, and —alkylene—aryl wherein the aryl portion contains 6 to 10 carbon atoms and the alkylene portion contains up to 6 carbon atoms; and a radical of the formula —Alk—Z wherein Alk is an alkylene, alkenylene or alkynylene group having up to 6 carbon atoms and wherein Z is selected from the group consisting of the unsubstituted, mono-substituted and poly-substituted cycloalkyl, cycloalkenyl, aryl, monoheterocyclic, polyheterocyclic and fused heterocyclic groups as defined above with respect to R;

and wherein n is a number from 1 to 6 inclusive.

DETAILED DESCRIPTION OF THE INVENTION

With respect to the various groups encompassed by the generic terms used here and throughout this specification, the following definitions and explanations are applicable:

The alkyl, alkenyl, alkynyl, alkylene, alkenylene and alkynylene groupings can be straight or branched-chain groups containing the aforementioned number of carbon atoms. Likewise, the alkyl portions of the alkylthio, alkoxy, alkanoyl, carbalkoxy, dialkylamino, alkanoyloxy, haloalkyl, alkylsulfonyl, alkylamino, carboxyalkyl, alkylcarbamoyl, dialkylcarbamoyl and alkanoylamino groupings each can be straight or branched-chain. The term "lower" used in conjunction with those groupings is intended to indicated that each alkyl portion therein can contain 1 to 8 carbon atoms. Similarly, when the word "lower" is used in conjunction with alkenyl and alkynyl, straight of branched-chain radicals containing 2 to 8 carbon atoms are contemplated.

Specific examples of alkyl radicals encompassed by formula (I), whether as a specific value for R, as a possible substituent on another R grouping, or as a portion of such a substituent, include methyl, ethyl, propyl, butyl, pentyl, hexyl, heptyl and octyl and their branched-chain isomers, as well as their straight and branched-chain higher homologues in the instances where "alkyl" can contain more than 8 carbon atoms. The alkenyl and alkynyl radicals can be exemplified by vinyl, propenyl, butenyl, ethynyl, propynyl, butynyl, and the like. Illustrative of the cycloalkyl and cycloalkenyl radicals are cyclopentyl, cyclohexyl and cyclopentenyl. The alkylene moieties are typified by methylene, ethylene, propylene, trimethylene, 1,2-butylene, 2,3-butylene, tetramethylene and the like. Exemplary of the contemplated alkenylene and alkynylene moieties are vinylene, ethynylene, butenylene and butynylene.

The alkylthio, alkoxy, alkanoyl, carbalkoxy, dialkylamino, alkanoyloxy, alkylsulfonyl, alkylamino, hydroxyalkyl, carboxyalkyl, alkylcarbamoyl, dialkylcarbamoyl and alkanoylamino groupings are of the type —S—alkyl
—O—alkyl —NH(alkyl)
—alkyl—OH
—alkyl—COOH and —NH—C—alkyl
      ‖
      O respectively, wherein alkyl is as hereinbefore defined and exemplified.

The term "aryl" as used herein is typified by phenyl and naphthyl.

The various heterocyclic moieties contemplated by the invention are generally attached to the —CHO portion of the RCHO grouping via a carbon-carbon bond. However, if the heterocycle is an N-heterocycle which contains an N atom having no double bond adjacent to it in the ring, then attachment to the —CHO may also be via a nitrogen-carbon bond.

When R comprises a heterocyclic function, representative heterocyclic moieties include piperazinyl, 4-methylpiperazinyl, 4-phenylpiperazinyl, pyridinyl, pyrazinyl, pyrimidinyl, pyridazinyl, pyrazolyl, pyrrolyl, pyrrolidinyl, pyrrolinyl, pyrazolinyl, pyrazolidinyl, piperidyl, morpholino, morpholinyl, quinuclidinyl, isoindolinyl, indolinyl, thienyl, benzothienyl, napthothienyl, thianthrenyl, furyl, pyranyl, chromenyl, xanthenyl, phenoxyathiinyl, imidazolyl, pyridyl, N-oxidopyridyl, indolizinyl, isoindolyl, 3H-indolyl, indolyl, indazolyl, purinyl, phthalazinyl, quinolyl, isoquinolyl, 4H-quinolizinyl, quinoxalinyl, naphthyridinyl, cinnolinyl, pteridinyl, carbazolyl, 4aH-carbazolyl, β-carbolinyl, phenanthridinyl, acridinyl, perimidinyl, phenoxazinyl, furazanyl, isochromanyl, chromanyl, imidazolinyl, 1-methylazarinyl, 1-methylpyrrolyl, 1-methylimidazolyl, 1-methylpyrazolyl, 2-methylisoindolyl, 3H-indolyl, phtalazinyl, quinoxilinyl, quinazidinyl, phenazinyl, isothiazolyl, 10-methylphenothiazinyl, isoxazolyl, furazanyl, imidazolinyl, 4-phenylpiperidino, piperidinyl, 4-benzylpiperidino, hexamethyleneimino, imidazolidinyl, and the various saturated, unsaturated or partially saturated congeners of any of the above. The same groups exemplify the Z portion of the —Alk—Z radicals encompassed by R when Z is heterocyclic.

With respect to the acyl groups encompassed by the R term, it is to be noted that R preferably represents an acyl radical selected from the group consisting of alkanoyl having 1 to 22 carbon atoms; alkenoyl having one or two double bonds and having 4 to 22 carbon atoms; cycloalkyl-having a total of 4 to 10 carbon atoms of which 3 to 7 are ring carbon atoms in the cycloalkyl portion and wherein m is zero, one or two; phenoxyacetyl; naphthalenecarbonyl; pyridinecarbonyl; and wherein m is zero, one or two and phenyl is unsubstituted or is substituted by 1 to 3 substituents, each of which may be alkyl having 1 to 4 carbon atoms, alkoxy having 1 to 4 carbon atoms, halo, trifluoromethyl, dialkylamino having 2 to 8 carbon atoms or alkanoylamino having 1 to 6 carbon atoms.

When R is alkanoyl containing 1 to 22 carbon atoms, there are included both unbranched and branched alkanoyl, for example, formyl, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl, docosanyl and 7,7-dimethyloctanoyl.

When R is alkenoyl having one or two double bonds and having 4 to 22 carbon atoms, there are included, for example, crotonyl, 9-octadecenoyl, 2,5-hexadienoyl, 3,6-octadienoyl, 10,13-octadecadienoyl and 5,13-docosadienoyl.

When R is there are included cycloalkanecarbonyl and cycloalkanealkanoyl groups wherein the cycloalkene portion can optionally bear 1 to 2 alkyl groups as substituents, e.g., cyclopropanecarbonyl, 1-methylcyclopropanecarbonyl, cyclopropaneacetyl, alphamethylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropylcyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When R is there are included, for example, benzoyl, phenylacetyl, alpha-phenylpropionyl, betaphenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, beta-(p-ethylphenyl)propionyl, p-anisoyl, m-anisoyl, o-anisoyl, m-isopropoxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, alpha-(m-bromophenyl)propionyl, p-trifluoromethylbenzoyl, 2,4-di(trifluoromethyl)benzoyl, m-trifluoromethylphenylacetyl, beta-(p-trifluoromethylphenyl)propionyl, 2-methyl-4-methoxybenzoyl, 3-chloro-4-ethoxybenzoyl, beta-(3-methyl-4-chlorophenyl)propionyl, p-dimethylaminobenzoyl, m-diethylaminobenzoyl, p-dibutylaminobenzoyl, p-(N-methyl-N-ethylamino)benzoyl, o-acetamidobenzoyl, m-propionamidobenzoyl, p-hexanoylaminobenzoyl, 3-chloro-4-acetamidophenylacetyl, and p-acetamidophenylpropionyl.

Where R is naphthalenecarbonyl, there are included 1-naphthalenecarbonyl and 2-naphthalenecarbonyl.

Where R is pyridinecarbonyl, there are included picolinoyl (2-pyridinecarbonyl), nicotinoyl (3-pyridinecarbonyl), and isonicotinoyl (4-pyridinecarbonyl).

The compounds of the present invention are conveniently prepared by reacting triamterene with an aldehyde of the formula RCHO wherein R is defined as hereinabove. Typically, the reactants are stirred together until a clear homogeneous solution is obtained (generally 0.5 hours to 4 days). The reaction is conveniently conducted at room temperature; however, the reaction mixture can be heated if so desired, in which case shorter reaction times are generally required. When the aldehyde is a liquid, it can very conveniently serve as the reaction solvent as well, particularly in instances where a large excess of aldehyde reactant is employed. Alternatively when the aldehyde is a liquid, and necessarily when the aldehyde is a solid, the reaction is conducted in a suitable non-reactive solvent, preferably a low-boiling polar solvent such as dioxane or tetrahydrofuran. Other useful non-reactive solvents (e.g. dimethylformamide) will be apparent to those skilled in the art, the solvent of choice depending on the particular aldehyde employed. When the reaction is complete, the solvent, if any, is removed by suitable means, e.g. distillation under reduced pressure, and the desired adduct is recovered from the reaction mixture. When excess aldehyde reactant has been employed as the solvent and upon completion of the reaction, the aldehyde and the desired adduct can be separated by trituration in a solvent in which the adduct is insoluble and the aldehyde is not. While ethyl ether is often appropriate for this purpose, the skilled organic chemist can readily determine an appropriate solvent for use in situations where ethyl ether is not.

In a preferred embodiment of the process for preparing the novel adducts of formula (I), a large molar excess (e.g., a ten-fold excess) of aldehyde to triamterene is employed. This process embodiment has generally been found convenient for preparing the 3:1 aldehyde:triamterene adducts, except in the case of formaldehyde, which tends to form a 6:1 adduct under the same conditions. It is possible to prepare adducts having other aldehyde:triamterene ratios by varying reaction conditions; thus, for example, using a much smaller ratio of aldehyde to triamterene reactant (e.g. about 1:1) would tend to favor formation of adducts having lower ratios than those obtained using excess aldehyde. However, as the 3:1 aldehyde:triamterene adducts have been found to possess a high degree of solubility and have given high plasma levels of triamterene following administration, the process preferably employs excess aldehyde reactant so as to favor formation of those 3:1 adducts. In many instances, use of excess aldehyde will eliminate any need for a separate solvent and thus also simplify separation of the final product.

The exact structure of the adducts of the present invention has not yet been determined. However, when analyzed according to the procedure to Example 1(b) below, the preferred adducts have been found to be those wherein n=3. This would suggest that the adduct is either a carbinolamine (II), an azomethine (III) or a complex between the pteridine and the aldehyde.

The IR spectra (KBr pellet) of the adducts shows an absence of aldehyde bands, apparently ruling out any type of non-covalently bonded molecular complex type of structure. The presence of broad absorption bands centered around 3400 cm$^{-1}$ indicates the presence of —OH and —NH groups in the molecule. Thus, the adduct is probably a carbinolamine.

While all of the compounds encompassed within the aforesaid generic formula (I) meet the objects of the present invention, nevertheless certain groups of compounds remain preferred, namely the adducts of triamterene with aldehydes wherein R is a monoheterocyclic moiety, particularly an unsaturated one (e.g. pyridyl, furyl, pyrrolyl) optionally substituted with methyl, hydroxy and/or hydroxymethyl; an alkyl radical, optionally substituted with halogen or hydroxy; a phenoxyalkyl group, optionally substituted with hydroxy; or a phenyl radical, optionally substituted with hydroxy. Particularly preferred among the foregoing are the 3:1 aldehyde:triamterene adducts because of their ease of preparation, high degree of solubility and ability to give high plasma levels of triamterene following administration. The preparation of preferred species of the invention is detailed in Example 1 below.

In order to further illustrate the present invention and the advantages thereof, the following specific examples are given, it being understood that same are intended only as illustrative and in nowise limitative.

EXAMPLE 1

(a) Preparation of the aldehyde adducts of triamterene.

3.0 Grams ($1.185 \times 10^{-2}$ moles) of triamterene were stirred at room temperature with a ten fold molar excess of the selected aldehyde. The mixture was stirred until a clear homogenous solution resulted (2 to 36 hours, depending on the particular aldehyde employed). That solution was then triturated in dry ethyl ether, and the precipitated solid was washed several times with the same solvent. The melting point and the triamterene content of the solid were determined after drying the material for at least 20 hours in vacuo.

(b) Determination of the triamterene content of the adducts.

The adduct formation of triamterene is an equilibrium process which can be shown as follows, wherein R"NH$_2$ is triamterene:

Thus, if a small amount (e.g. 15–20 mg) of the adduct is put in solution, it should degrade to yield triamterene and the aldehyde. Therefore, in order to measure the amount of triamterene in the adducts, small amounts of the adducts were degraded to triamterene in solution, and the concentration of the drug was determined by liquid chromatography.

A carefully weighed amount of the adduct (15–20 mg) was dissolved in a small amount of methanol (5–10 ml) and distilled water was added to make a final volume of 100 ml. That solution was then chromatographed on a high pressure liquid chromatograph (a reverse phase Chrompack Lichrosorb 10 RP 18 column, length=25 cm, i.d.=4.6 mm) using as the eluting solvent a mixture consisting of 70% methanol, 25% water and 5% glacial acetic acid, $5.0 \times 10^{-3}$ M in octylsulfonic acid. The resulting peak height for triamterene was compared to a standard curve for triamterene to yield the concentration of the drug in the prepared solution. Comparison of the concentration of the drug in the solution of the adduct, to the amount of adduct weighed out, gave the percentage of triamterene in the adduct.

Adducts of triamterene with formaldehyde, acetaldehyde, propionaldehyde, butyraldehyde, trichloroacetaldehyde, 4-pyridinecarboxyaldehyde (isonicotinaldehyde) and 2-pyridinecarboxaldehyde (picolinaldehyde) were prepared and analyzed as described in (a) and (b) above. The results are tabulated below.

TABLE I

ALDEHYDE ADDUCTS OF TRIAMTERENE

| Aldehyde | m.p. (°C.) | % Triamterene | Molar Ratio* |
|---|---|---|---|
| Formaldehyde | 85–90 | 58.1 | 6 |
| Acetaldehyde | 180 (decomposition) | 65.7 | 3 |
| Propionaldehyde | glass | | |
| Butyraldehyde | 120 | 54.0 | 3 |
| Trichloroacetaldehyde | 85–89 | 36.5 | 3 |
| 4-Pyridinecarboxaldehyde | 78–79 | 42.0 | 3 |

TABLE I-continued

| ALDEHYDE ADDUCTS OF TRIAMTERENE | | | |
|---|---|---|---|
| Aldehyde | m.p. (°C.) | % Triamterene | Molar Ratio* |
| 2-Pyridinecarboxaldehyde | 110 | 42.5 | 3 |

*Molar ratio of aldehyde to triamterene in adduct

EXAMPLE 2

Using the general procedure detailed in Example 1(a), modified where necessary by first placing the reactants in an appropriate solvent such as dioxane or tetrahydrofuran, the 3:1 adducts of the following aldehydes can be prepared:
  phenoxyacetaldehyde
  p-hydroxyphenoxyacetaldehyde
  salicylaldehyde (o-hydroxybenzaldehyde)
  p-hydroxybenzaldehyde
  m-hydroxybenzaldehyde
  pyridoxal
  α,α,β-trichlorobutyraldehyde
  furfural (2-furaldehyde)
  pyrrole-2-carboxaldehyde
  glyceraldehyde 3-phosphate

EXAMPLE 3

Four adult beagle dogs, ranging in weight from 16 to 22 pounds, were used to assess the relative bioavailability of triamterene administered as representative triamterenealdehyde adducts of the present invention compared to the commercially available formulation of triamterene, DYRENIUM®, and to triamterene suspended in 10 ml of 0.125% aqueous solution of Gum Tragacanth.

The aldehyde adducts were administered as solutions in PEG 400 (polyethylene glycol having an average molecular weight between 380 and 420) in soft gelatine capsules. The amounts of the adducts administered were the molar equivalents of 50 mg triamterene. For comparison purposes, 50 mg of triamterene as DYRENIUM®, and a suspension of 50 mg triamterene and 125 mg of Gum Tragacanth in 10.0 ml of distilled water, were also administered. Venous blood was withdrawn into 4 ml Vacutainers containing 3 mg EDTA (ethylenediaminetetraacetic acid), at appropriate time intervals following the dose. The blood samples were immediately centrifuged, and the separated plasma was kept at −18° C. until analysis. The analytical procedure was as follows:

To 0.50 ml of plasma in a 15 ml screw cap centrifuge tube, 0.25 ml of 3 M perchloric acid was added. After mixing briefly on a vortex mixer, 1.0 ml of methyl isobutyl ketone was added and the mixture was centrifuged for 7 minutes at 2500 revolutions per minute using a table centrifuge. An aliquot of exactly 50 μg was used for chromatographic analysis.

The chromatographic equipment consisted of a Waters Model 6000A pump and a U6K injector, a Chrompack Lichrosorb 7-Si-60 normal phase silica column eluted with a 55:35:10:0.10 mixture of dichloromethane-heptane-methanol-70% perchloric acid at a flow rate of 2.0 ml/minute, and a Schoeffel Model LS 790 Fluorescence detector with the emission monitored using a sharp cut filter at 470 nm and the excitation set at 335 nm.

Figure 1:
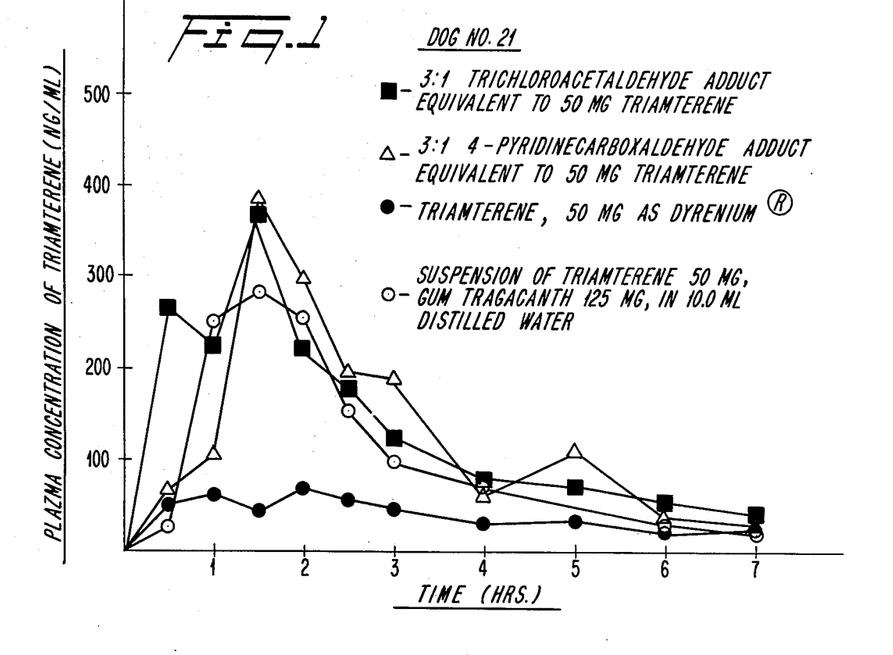
FIGS. 1 and 3 are each a graph of the plasma concentration of triamterene in ng/ml, versus time, observed when the drug was administered to a dog as DYRENIUM ®; as a suspension of triamterene in Gum Tragacanth; as a 3:1 trichloroacetaldehyde adduct with triamterene; and as a 3:1 4-pyridinecarboxaldehyde adduct with triamterene.
Figure 2:
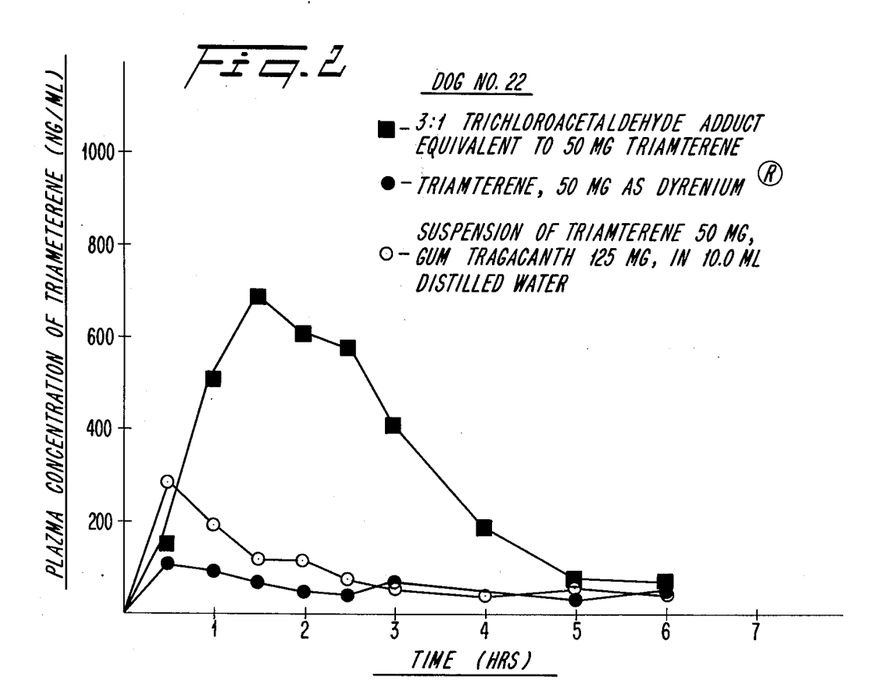
FIG. 2 is a graph of the plasma concentration of triamterene in ng/ml, versus time, observed when the drug was administered to a dog as DYRENIUM ®; as a 3:1 trichloroacetaldehyde adduct with triamterene; and as a suspension of triamterene in Gum Tragacanth.
Figure 3:
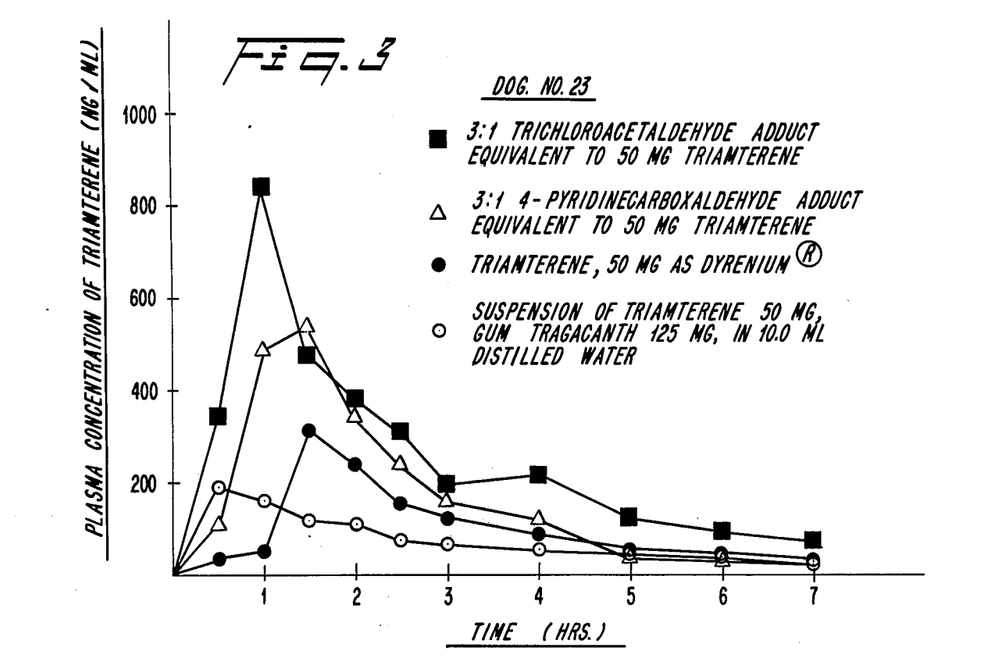
Figure 4:
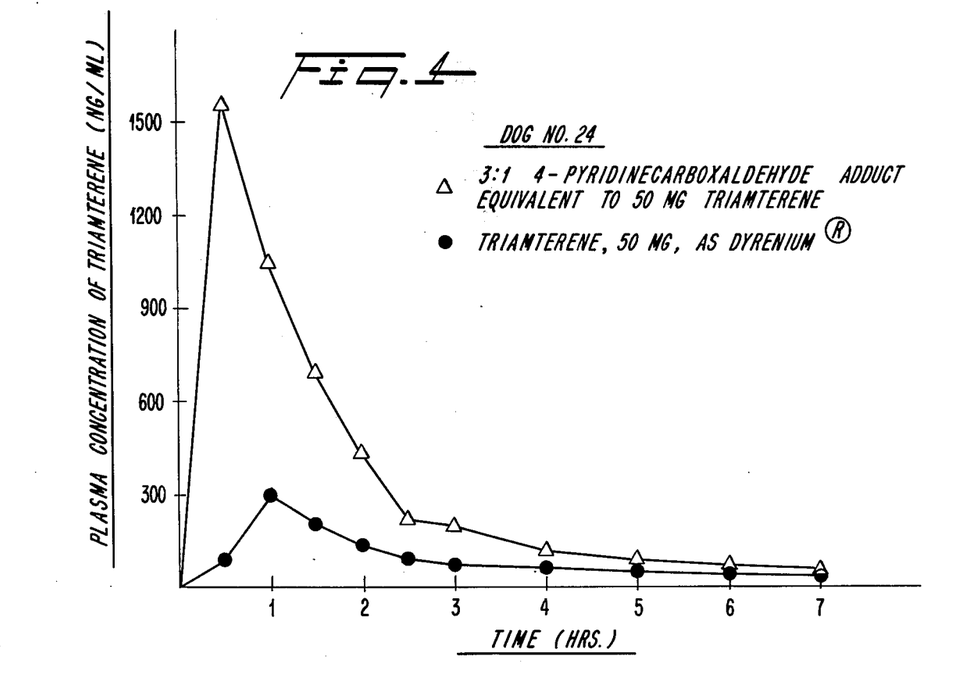
FIG. 4 is a graph of the plasma concentration of triamterene in ng/ml, versus time, observed when the drug was administered to a dog as triamterene, and as a 3:1 4-pyridinecarboxaldehyde adduct with triamterene.

FIGS. 1 through 4 show the plasma levels of triamterene measured as described above following the administration of various dosage forms of triamterene and representative adducts of the present invention. From these figures, the relative areas under the curve for triamterene and the various aldehyde adducts were calculated. The results of those calculations are set forth in Table II below.

TABLE II

| | | Area under the Curve (nghr/ml) | | |
|---|---|---|---|---|
| Compound | Dog No. | | AUC | Relative AUC |
| Triamterene as | 21 | | 260.5 | |
|  | 22 | | 353.3 | |
| DYRENIUM® 50 mg | 23 | | 668.6 | |
|  | 24 | | 502.5 | |
| Mean ± SEM | | 446 ± | 100 | 1 |
| Triamterene Suspension | 21 | | 739.3 | |
|  | 22 | | 541.0 | |
|  | 23 | | 548.3 | |
| Mean ± SEM | | 610 ± | 65 | 1.36 |
| Trichloroacetaldehyde | 21 | | 959.3 | |
| 3:1 adduct | 22 | | 1882.7 | |
|  | 23 | | 1741.9 | |
| Mean ± SEM | | 1528 ± | 287 | 3.43 |
| 4-Pyridinecarboxaldehyde | 21 | | 876.4 | |
|  | 23 | | 1212.1 | |
|  | 24 | | 2296.0 | |
| Mean ± SEM | | 1462 ± | 428 | 3.28 |

The novel adducts of formula (I) can be conveniently administered orally or parenterally (I.V., I.P. or I.M.) by simply combining a therapeutically effective amount thereof with any pharmaceutically acceptable non-toxic oral or parenteral carrier. The carrier may be, for example, a solid or liquid. If a liquid carrier is used, e.g. peanut oil, olive oil, sesame oil or water, the preparation can be prepared in the form of a solution, suspension or syrup, and can optionally be placed in a gelatin capsule. If a solid carrier is used, the preparation can be tableted, placed in a capsule, etc. Suitable solid carriers may include lactose, starch (pharmaceutical grade), dicalcium phosphate, calcium sulfate, kaolin, mannitol, and powdered sugar. In addition, when required, suitable binders, lubricants, disintegrating agents, and coloring agents can also be added to the oral dosage form. Typical binders include starch, gelatin, sugars, such as sucrose, molasses, and lactose, natural and synthetic gums, such as acacia, sodium alginate, extract of Irish moss, carboxymethylcellulose, methyl cellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include without limitation, starch, methylcellulose, agar, bentonite, cellulose and wood products, alginic acid, guar gum, citrus pulp, carboxymethylcellulose, and sodium lauryl sulfate. If desired, a conventional pharmaceutically acceptable dye can be incorporated into the dosage unit form.

In the compositions described above, the active ingredient of formula (I) will be present in an amount envisioned to produce the desired result. Naturally, the therapeutic dosage range for the adducts of the instant invention will vary with the particular adduct employed and the size and needs of the patient. Generally speaking however, the dose will be less than or equal to the equivalent on a molar basis of the required dose of the parent drug, triamterene. In general, because the instant adducts provide much greater plasma levels of triamterene than equivalent doses of triamterene itself, therapeusis can be achieved at a fraction of the dosages of triamterene usually employed.

In veterinary practice, the adducts or compositions described above can be administered per se or can be added to the animal's food or water supply.

The pharmaceutical and veterinary compositions containing the instant adducts may contain additional medicinal ingredients such as vitamins or other diuretics. In a preferred embodiment, an adduct of the present invention is present in combination with a non-pteridine diuretic in any of the above-described pharmaceutical or veterinary compositions. Suitable non-pteridine diuretics for use in such combination products include ethacrynic acid and sodium ethacrynate; thiazide diuretics (including their analogs) such as bendroflumethiazide, benzthiazide, chlorothiazide, chlorothiazide sodium, cyclothiazide, flumethiazide, hydrochlorothiazide, hydroflumethiazide, methyclothiazide, polythiazide, quinethazone, trichloromethiazide, althiazide, buthiazide, cyclopenthiazide, epithiazide, methalthiazide and metolazone; and other sulfonamide derivatives such as bumetanide, furosemide, chlorthalidone, alipamide, chlorexolone, diapamide, ambuside, clopamide, mefruside and xipamide. In general, any non-pteridine diuretic which causes potassium loss can thus be beneficially combined with the potassium-saving adducts of the present invention. Obviously, when both the adduct and a non-pteridine diuretic are to be administered to a patient, such can be accomplished by means of separate dosage forms as well as in a single combination product.

From the foregoing description, one of ordinary skill in the art can easily ascertain the essential characteristics of the instant invention, and without departing from the spirit and scope thereof, can make various changes and/or modifications of the instant invention to adapt it to various usages and conditions. As such, these changes and/or modifications are properly, equitably and intended to be, within the full range of equivalence of the following claims.

What we claim is:

1. An aldehyde adduct of triamterene having the formula:

wherein R is selected from the group consisting of:
hydrogen;
alkyl of 1 to 20 carbon atoms;
cycloalkyl of 3 to 8 carbon atoms;
phenyl;
naphthyl;
alkenyl of 2 to 20 carbon atoms;
alkynyl of 2 to 20 carbon atoms;
cycloalkenyl of 4 to 8 carbon atoms;
alkanoyl having 1 to 22 carbon atoms;
alkenoyl having one or two double bonds and having 4 to 22 carbon atoms;

having a total of 4 to 10 carbon atoms of which 3 to 7 are ring atoms in the cycloalkyl portion and wherein m is zero, one or two and cycloalkyl is unsubstituted or is substituted by 1 or 2 lower alkyl groups;
phenoxyacetyl;
1-naphthalenecarbonyl;
2-naphthalenecarbonyl;
2-pyridinecarbonyl;
3-pyridinecarbonyl;
4-pyridinecarbonyl;

wherein m is zero, one or two and phenyl is unsubstituted or is substituted by 1 to 3 substituents, each of which may be alkyl having 1 to 4 carbon atoms, alkoxy having 1 to 4 carbon atoms, halo, trifluoromethyl, dialkylamino having 2 to 8 carbon atoms or alkanoylamino having 1 to 6 carbon atoms;
substituted phenyl and naphthyl having 1 to 3 substituents, which may be the same or different, each of which is selected from the group consisting of lower alkylthio, lower alkyl, halo, lower alkoxy, nitro, cyano, lower alkanoyl, lower carbalkoxy, di(lower alkyl)amino, lower alkanoyloxy, lower haloalkyl, lower alkylsulfonyl, hydroxy, lower hydroxyalkyl, amino, lower alkanoylamino, lower alkylamino, carboxyl, lower carboxyalkyl, carbamoyl, lower alkylcarbamoyl, di(lower alkyl)carbamoyl, lower alkenyl, lower alkynyl, oxo, and -alkylene-aryl wherein the aryl portion is phenyl or naphthyl and the alkylene portion has up to 6 carbon atoms;
substituted alkyl, cycloalkyl, alkenyl, alkynyl and cycloalkenyl wherein alkyl, cycloalkyl, alkenyl, alkynyl and cycloalkenyl are as defined above with respect to R, having 1 to 3 substituents, which may be the same or different, each of which is selected from the group consisting of halo, hydroxy, lower alkoxy, carboxy, oxo, lower alkanoyloxy, phenoxy, naphthoxy, and substituted phenoxy and naphthoxy having 1 to 3 substituents, which may be the same or different, each of which is selected from the group of substituents defined above with respect to substituted phenyl and naphthyl;
saturated and unsaturated heterocyclic groups of 1 to 3 rings, at least one of said rings containing from 1 to 3 of any one or more of the hetero atoms N, S and O, each of said rings being 3- to 8-membered, all ring atoms in each of said rings which are other than N, S and O being carbon, with the proviso that when there are 2 or 3 of said rings, then said rings are fused;
substituted derivatives of the aforesaid heterocyclic groups having 1 to 3 substituents, which may be the same or different, each of which is selected from the group consisting of lower alkyl, lower haloalkyl, halo, amino, oxo, nitro, hydroxy, lower hydroxyalkyl, carboxyl, lower carboxyalkyl, lower alkanoylamino, lower alkoxy, lower alkanoyl, lower alkanoyloxy, cyano, lower carbalkoxy, lower alkylthio, lower alkylamino, di(lower alkyl)amino, carbamoyl, lower alkylcarbamoyl, di(lower alkyl)carbamoyl, lower alkenyl, lower alkynyl, lower alkylsulfonyl, phenyl, naphthyl, and -alkylene-aryl wherein the aryl portion is phenyl or naphthyl and the alkylene portion has up to 6 carbon atoms; and a radical of the formula —Alk—Z wherein Alk is an alkylene, alkenylene or alkynylene group having up to 6 carbon atoms and wherein Z is selected from the group consisting of the unsubstituted and substituted cycloalkyl, cycloalkenyl, phenyl, naphthyl, and heterocyclic groups as defined above with respect to R;

and wherein n is a number from 1 to 3 inclusive, with the proviso that when R is hydrogen, than n can be a number from 1 to 6 inclusive.

2. An adduct of claim 1 wherein R is hydrogen.
3. An adduct of claim 1 wherein R is alkyl.
4. An adduct of claim 1 wherein R is cycloalkyl.
5. An adduct of claim 1 wherein R is phenyl or naphthyl.
6. An adduct of claim 1 wherein R is alkenyl.
7. An adduct of claim 1 wherein R is alkynyl.
8. An adduct of claim 1 wherein R is cycloalkenyl.
9. An adduct of claim 1 wherein R is alkanoyl.
10. An adduct of claim 1 wherein R is substituted phenyl.
11. An adduct of claim 1 wherein R is substituted alkyl.
12. An adduct of claim 1 wherein R is substituted cycloalkyl.
13. An adduct of claim 1 wherein R is substituted alkenyl.
14. An adduct of claim 1 wherein R is substituted alkynyl.
15. An adduct of claim 1 wherein R is substituted cycloalkenyl.
16. An adduct of claim 1 wherein R is a saturated or unsaturated heterocyclic group having 1 ring.
17. An adduct of claim 1 wherein R is a saturated or unsaturated heterocyclic group having 2 or 3 rings.
18. An adduct of claim 1 wherein R is a substituted derivative of a saturated or unsaturated heterocyclic group having 1 ring.
19. An adduct of claim 1 wherein R is a substituted derivative of a saturated or unsaturated heterocyclic group having 2 or 3 rings.
20. An adduct of claim 1 wherein R is a radical of the formula —Alk—Z.
21. An adduct of claim 5 wherein R is phenyl.
22. An adduct of claim 1 wherein R is selected from the group consisting of alkanoyl having 1 to 22 carbon atoms; alkenoyl having one or two double bonds and having 4 to 22 carbon atoms;

having a total of 4 to 10 carbon atoms of which 3 to 7 are ring carbon atoms in the cycloalkyl portion and wherein m is zero, one or two and cycloalkyl is unsubstituted or is substituted by 1 or 2 lower alkyl groups; phenoxyacetyl; 1-napthalenecarbonyl; 2-naphthalenecarbonyl; 2-pyridinecarbonyl; 3-pyridinecarbonyl; 4-pyridinecarbonyl; and wherein m is zero, one or two and phenyl is unsubstituted or is substituted by 1 to 3 substituents, each of which may be alkyl having 1 to 4 carbon atoms, alkoxy having 1 to 4 carbon atoms, halo, trifluoromethyl, dialkylamino having 2 to 8 carbon atoms or alkanoylamino having 1 to 6 carbon atoms.

23. An adduct of claim 10 wherein R is hydroxy-substituted phenyl.
24. An adduct of claim 11 wherein R is hydroxy-substituted alkyl.
25. An adduct of claim 11 wherein R is halogen-substituted alkyl.
26. An adduct of claim 11 wherein R is phenoxy-substituted alkyl.
27. An adduct of claim 11 wherein R is hydroxyphenoxy-substituted alkyl.
28. An adduct of claim 16 wherein R is an unsaturated monoheterocyclic group.
29. An adduct of claim 28 wherein R is pyridyl.
30. An adduct of claim 28 wherein R is furyl.
31. An adduct of claim 28 wherein R is pyrrolyl.
32. An adduct of claim 16 wherein R is a substituted unsaturated one ring heterocyclic group having 1 to 3 substituents, which may be the same or different, selected from the group consisting of hydroxy, methyl, and hydroxymethyl.
33. An adduct of claim 1 wherein n is 3.
34. An adduct of claim 3, 5, 23, 24, 25, 26, 27, 28, 29, 30, 31, or 32 wherein n is 3.
35. The adduct of claim 1 which is the 6:1 adduct of formaldehyde and triamterene.
36. The adduct of claim 1 which is the 3:1 adduct of acetaldehyde and triamterene.
37. The adduct of claim 1 which is the 3:1 adduct of propionaldehyde and triamterene.
38. The adduct of claim 1 which is the 3:1 adduct of butyraldehyde and triamterene.
39. The adduct of claim 1 which is the 3:1 adduct of trichloroacetaldehyde and triamterene.
40. The adduct of claim 1 which is the 3:1 adduct of 4-pyridinecarboxaldehyde and triamterene.
41. The adduct of claim 1 which is the 3:1 adduct of 2-pyridinecarboxaldehyde and triamterene.
42. The adduct of claim 1 which is the 3:1 adduct of phenoxyacetaldehyde and triamterene.
43. The adduct of claim 1 which is the 3:1 adduct of p-hydroxyphenoxyacetaldehyde and triamterene.
44. The adduct of claim 1 which is the 3:1 adduct of salicylaldehyde and triamterene.
45. The adduct of claim 1 which is the 3:1 adduct of p-hydroxybenzaldehyde and triamterene.
46. The adduct of claim 1 which is the 3:1 adduct of m-hydroxybenzaldehyde and triamterene.
47. The adduct of claim 1 which is the 3:1 adduct of pyridoxal and triamterene.
48. The adduct of claim 1 which is the 3:1 adduct of α,α,β-trichlorobutyraldehyde and triamterene.
49. The adduct of claim 1 which is the 3:1 adduct of furfural and triamterene.
50. The adduct of claim 1 which is the 3:1 adduct of pyrrole-2-carboxaldehyde and triamterene.
51. The adduct of claim 1 which is the 3:1 adduct of glyceraldehyde 3-phosphate and triamterene.
52. A pharmaceutical composition having diuretic or hypotensive activity comprising an effective diuretic or hypotensive amount of an adduct of claim 1, in combination with a pharmaceutically acceptable non-toxic carrier.

53. A pharmaceutical composition of matter having diuretic and potassium-saving activity comprising an effective diuretic amount of a non-pteridine diuretic and an effective potassium-saving amount of an adduct of claim 1, in combination with a pharmaceutically acceptable non-toxic carrier.

54. A pharmaceutical composition of claim 53 wherein the non-pteridine diuretic is ethacrynic acid or sodium ethacrynate.

55. A pharmaceutical composition of claim 53 wherein the non-pteridine diuretic is a thiazide diuretic.

56. A pharmaceutical composition of claim 55 wherein the thiazide diuretic is selected from the group consisting of bendorflumethiazide, benzthiazide, chlorothiazide, cyclothiazide, flumethiazide, hydrochlorothiazide, hydroflumethiazide, methyclothiazide, polythiazide, quinethazone and trichloromethiazide.

57. A pharmaceutical composition of claim 53 wherein the non-pteridine diuretic is selected from the group consisting of bumetanide, chlorthalidone and furosemide.

58. A pharmaceutical composition of claim 53 wherein the non-pteridine diuretic is selected from the group consisting of alipamide, chlorexolone, diapamide, ambuside, clopamide, mefruside and xipamide.

59. A method of eliciting a diuretic or hypotensive response in a warm-blooded animal which comprises administering thereto an effective diuretic or hypotensive amount of an adduct of claim 1, in combination with a pharmaceutically acceptable non-toxic carrier.

60. A method of eliciting a diuretic response in a warm-blooded animal without accompanying substantial loss of potassium which comprises administering to said animal an effective diuretic amount of a non-pteridine diuretic and an effective potassium-saving amount of an adduct of claim 1, in combination with a pharmaceutically acceptable non-toxic carrier.

* * * * *